United States Patent [19]

Conner, Jr. et al.

[11] 4,302,610
[45] Nov. 24, 1981

[54] VANADIUM CONTAINING NIOBATES AND TANTALATES

[75] Inventors: William C. Conner, Jr., Montague, Mass.; Stuart L. Soled, Madison, N.J.; Anthony J. Signorelli, Succasunna, N.J.; Bruce A. DeRites, Wayne, N.J.

[73] Assignee: Allied Corporation, Morris Township, Morris County, N.J.

[21] Appl. No.: 153,483

[22] Filed: May 27, 1980

[51] Int. Cl.³ .................... C07C 27/12; C07C 45/32; C07C 49/04

[52] U.S. Cl. .................. 568/475; 568/399; 568/910

[58] Field of Search ............... 568/475, 911, 910, 399

[56] References Cited

U.S. PATENT DOCUMENTS

| | | | |
|---|---|---|---|
| 3,806,470 | 4/1974 | Aykan | 252/462 |
| 3,843,553 | 10/1974 | Aykan | 252/464 |
| 3,902,985 | 9/1975 | Raetzsch | 204/268 |
| 4,057,474 | 11/1977 | Kurtz | 204/98 |
| 4,177,161 | 12/1979 | Umemura et al. | 252/435 |
| 4,181,587 | 1/1980 | Kurtz | 204/98 |
| 4,195,188 | 3/1980 | Slinkard et al. | 568/475 |
| 4,197,179 | 4/1980 | Ezzell et al. | 204/255 |
| 4,219,671 | 8/1980 | Slinkard | 568/475 |

OTHER PUBLICATIONS

Bordes et al. "Jour. of Catalysis" vol. 57, pp. 236-252, (1979).

*Primary Examiner*—Werren B. Lone
*Attorney, Agent, or Firm*—Alan M. Doernberg; Gerhard H. Fuchs

[57] ABSTRACT

Compositions having a host phase of a niobate or tantalate of a divalent or trivalent metal and containing vanadium from one atom present to the limit of solid solubility in the host phase. Host phases of the rutile, columbite and trirutile structure are disclosed. The compositions are useful in the partial oxidation and ammoxidation of lower alkanes.

16 Claims, No Drawings

VANADIUM CONTAINING NIOBATES AND TANTALATES

DESCRIPTION

Field of the Invention

The present invention relates to vanadium-containing niobates and tantalates, their preparation and their use as catalysts in the gas phase oxidation and/or ammoxidation of alkanes and alkenes.

BACKGROUND OF THE INVENTION

The gas phase oxidation of alkanes and alkenes can lead to oxidation products which are more valuable then the starting compounds.

K. Aykan et al. in U.S. Pat. No. 3,843,553 issued Oct. 22, 1974 disclose catalyst compositions of Scheelite crystal structure containing bismuth ions, divalent ions and cation vacancies.

K. Aykan et al. in U.S. Pat. No. 3,806,470 issued Apr. 23, 1974 disclose catayst compositions of Scheelite crystal structure containing certain ions having ionic radii in the range of about 0.9 A to about 1.6 A.

Vanadium-phosphorous catalysts have been disclosed for the oxidation of butane to maleic anhydride in several references including E. Bondes et al., *J. Catal.*, vol. 57, pp. 236 et. seq. (1979).

Addition of vanadium to an Sb-Mo-O system to produce a catalyst for propylene and isobutylene oxidation is disclosed in *Chem. Abstr.* 77:163919k.

These references are representative of the art with regard to heterogeneous catalyzation of hydrocarbon oxidation.

Zolotukhina et. al. disclose properties of $Cr_xNb_xV_{2-2x}O_4$ and $Fe_xNb_xV_{2-2x}O_4$ ($0<x<0.09$) solid solutions in articles abstracted at *Chem. Abstr.* 88:113568b, 88:129496n and 88:56771m.

In the rutile structure every metal atom is surrounded by six oxygen neighbors and each oxygen has three metal ion neighbors. Strings of edge sharing $MO_6$ octahedra extend along one direction and are connected to adjacent strings by corner sharing.

The unit cell of the trirutile structure corresponds to three unit cells of the simple rutile structure wherein the metal positions are occupied in an ordered way by two pentavalent and one divalent metal ions or two trivalent and one hexavalent metal ions. The columbite structure is related to the trirutile structure in that the metal coordination remains octahedral and the metal atoms are ordered in an analogous manner. They differ, however, in that the strings of edge shared octahedra form a zig-zag pattern in the columbite structure and run in straight chains in the trirutile structure.

SUMMARY OF THE INVENTION

Niobates and/or tantalates of two valent metals are provided having an atom ratio of oxygen to total metal of from about 1.8 to 2.2 and containing vanadium from about one atom percent to the limit of solid solubility in the host phase. The host phases preferably have trirutile, rutile or columbite crystal structure. Host phase means in the context of the present invention a phase type not containing vanadium.

A method is provided for preparing the above niobates and/or tantalates comprising mixing precursor metal compounds and reacting the mixture at temperatures between 700° C. and 1000° C. in an inert atmosphere.

The niobates and/or tantalates are employed as catalysts in a method for oxidizing or ammoxidizing lower alkanes or alkenes comprising passing a mixture of lower alkane or alkenes and oxygen over the catalyst for obtaining oxidized alkanes or alkenes. Such oxidized alkanes or alkenes include valuable organic intermediates and solvents e.g. formaldehyde, acetaldehyde, acrolein, ethanol, glycol, allyl alcohol and glycerol.

DETAILED DESCRIPTION OF THE INVENTION

Catalyst Preparation

In accordance with the present invention there is provided a method for preparing niobate and/or tantalates comprising mixing precursor metal compounds and reacting the mixture.

Precursor materials include oxides, acetates, carbonates, formates, nitrates, sulfates, sulfites and other metal derivatives which can be transformed into oxides, e.g. by heat treatment.

Metals for forming part of the niobates and/or tantalates of the present invention include Mg, Zn, Cd, Ca, Al, Sc, Ga, Ca, Cr, Mn, Fe, Co, Ni.

The niobates and/or tantalates of the present invention contain from about 1 atom percent vanadium to the limiting amount still forming a solid solution but usually not more than about 20 atomic percent.

The atom percent of vanadium is calculated by taking the moles of V, dividing the moles of total metal and multiplying by 100.

Preferably the amount of vanadium is from about 2 to 10 atom percent.

The atomic ratio of oxygen to total metal in the niobates and/or tantalates of the present invention is from about 1.8 to about 2.2 and preferably from about 1.9 to about 2.1.

The crystal structures of the niobates and/or tantalates useful according to the present invention include the rutile, trirutile and columbite type.

Preferred niobates and/or tantalates of the present invention having a trirutile structure include compositions of the formulae $M\ Nb_2O_6 \cdot n\ VO_2$
$M\ Ta_2O_6 \cdot n\ VO_2$ wherein n=0.01 to 0.2 and M can be Mg, Cd, Ca, Mn, Fe, Co, or Ni.

Preferred niobates and/or tantalates of the present invention having a columbite structure include compositions of the formulae $M\ Nb_2O_6 \cdot m\ VO_2$
$M\ Ta_2O_6 \cdot m\ VO_2$ wherein m=0.01 to 1 and M can be Mg, Zn, Cd, Ca, or Mn. Preferred niobates and/or tantalates having the rutile structure include $M_{1.5}Nb_{1.5}O_6 \cdot p\ VO_2$
$M_{1.5}Ta_{1.5}O_6 \cdot p\ VO_2$ wherein p=0.01 to 0.5 and M can be Mg, Zn, Ca, Mn, Fe, Co, or Ni.

Preferred compositions according to the present invention include:

$FeTa_2O_6 \cdot 0.2VO_2$ (trirutile)
$CoTa_2O_6 \cdot 0.2VO_2$ (trirutile)
$NiTa_2O_6 \cdot 0.2VO_2$ (trirutile)
$ZnTa_2O_6 \cdot 0.2VO_2$ (columbite)

FeNb$_2$O$_6$.0.2VO$_2$ (columbite)

The niobates and/or tantalates of the present invention can be prepared by heating intimate mixtures of precursors of the desired metal oxide composition and proportion to temperatures from 400° C. to about 1300° C. with a preferred temperature of 600° C. to 950° C. The reaction time can vary and is in general from about 10 min. to 10 days, and preferably from 1 hour to 5 hours. The intimite mixtures of precursors are obtainable by mixing solid metal derivatives of the desired proportion of metals or by decomposing precursor mixtures followed by renewed mixing. Mixing can be achieved by grinding the solids in a mill.

The reaction atmosphere is in general inert. The reaction to the niobate and/or tantalates containing vanadium can be performed in a vacuum or in an inert atmosphere such as argon, nitrogen and the like. A vacuum is preferred.

The resulting niobate and/or tantalate compositions can be analytically confirmed. The phases present can be examined with x-rays. Crystallographic order can be detected by the appearance of superstructure reflections.

Furthermore niobates and tantalates of trivalent chromium, iron, magnanese and aluminum having composition of either of the following formulae M'NbO$_4$.q VO$_2$
M'TaO$_4$.q VO$_2$ wherein q=0.01 to 0.05 and
M'=Cr, Fe, Mn, Al are also useful in the oxidation and ammoxidation of alkanes and/or alkenes. They are prepared by the technique disclosed above with the exception of providing a different starting composition to contribute M' and to provide more oxygen, and they are employed in the same way as catalysts as the niobates and/or tantalates of divalent metals.

Oxidation and Ammoxidation of Alkanes and/or Alkenes

The niobates and/or tantalates of the present invention can be employed in the oxidation and ammoxidation of alkanes and/or alkenes.

Alkanes and/or alkenes useful as starting materials include those having from about 2 to 20 carbon atoms. They can be straight chain, branched, or cyclic alkanes or alkenes.

The oxidizing agent can be air, oxygen, nitrous oxides, halooxides or ozone. Air is the preferred oxidizing agent.

The oxidation can be performed in the presence of ammonia vapor as ammoxidation.

The molar ratio of hydrocarbon to oxidizing agent can be from about 4:1 to 1:1.

The temperature for the oxidation reaction is from about 300° C. to 600° C.

There is a preferred lower temperature range of from about 320° C. to 420° C. and a preferred higher temperature range from about 450° C. to 500° C.

The reaction pressure is not critical and can, for example, be from about one to ten atmospheres (100 to 1000 kPa).

The contact time is not critical and can, for example, be from about 1 second to 10 seconds.

The space velocity is defined as the volume of gas passing over the volume of catalyst per hour. While not critical, preferably, the space velocity is from about 1000 to 10000 hr$^{-1}$.

The reactor can be any type suitable for heterogeneous catalytic reactions in the gas phase.

Preferred reactors include fixed bed and fluidized bed reactors. Preferably the temperature in the reactor and the pressure in the reactor are automatically controlled.

After use the niobate and/or tantalate catalyst can be removed from the reactor and be replaced by fresh catalyst. Normally the catalyst does not deactivate.

Reaction Products

The reaction products depend on the reaction conditions. They include cracked, and dehydrogenated and oxidized alkanes and alkenes. The carbonyl function can occur in a large part of the reaction products.

The resulting output gas mixture can be analyzed as to its compounds by methods such as mass spectroscopy and gas chromatography. The components can be separated by conventional methods such as distillation.

The hydrocarbon conversion is defined as the ratio of the difference of the number of moles of alkane/alkene input minus the number of alkane/alkene output divided by the number of moles of alkane/alkene input.

The normalized number of moles of a particular product is defined as the number of moles of the product multiplied by the ratio of the number of carbon atoms in the particular product molecule divided by the number of carbon atoms in the starting material molecules.

The selectivity to a particular product is defined as the normalized number of moles of that particular product divided by the total normalized number of moles of the products obtained.

The specific selectivity is the normalized number of moles of product of partially oxidized molecules divided by the sum or normalized moles of all products of partially oxidized molecules.

Vanadium substituted niobates and/or tantalates with rutile-related structure provide high selectivities in the formation of methanol and acetaldehyde of about 20% and 15% respectively with a conversion of the input hydrocarbon of about 25%. Rutile related materials containing zinc, tantalum and vanadium provide selectivities to methanol and acetaldehyde of similar magnitude but enhanced amounts of propane are cracked at the same times.

The products in the case of ammoxidation include amino and nitrilo groups resulting in products such as methylamine, acetonitrile and acrylonitrile.

The resulting products are useful as solvents and building blocks for the synthesis of organic compounds.

EXAMPLES 1-8

Preparation of Niobates and/or Tantalates

Niobates and/or tantalates were prepared via high temperature reaction (600°-950° C.) of the component oxides or carbonates. The powders were ground between successive heating cycles to ensure homogeneity. To stabilize subvalent oxidation states, the oxides were reacted with a reducing agent (i.e. the metal itself) in an evacuated, sealed quartz ampoule. For example, zinc oxide (0.01 mol, 0.8 g) was mixed with tantalum pentoxide (0.01 mol, 4.4 g), vanadium pentoxide (0.0008 mol, 0.145 g) and vanadium metal (0.0004 mol, 0.02 g). The mixture was placed in an evacuated, sealed ampoule and placed in a 800° C. oven for 24 h. After cooling to room temperature, the material was ground thoroughly in an inert atmosphere and again placed in an evacuated, sealed ampoule. The process was repeated through three heating and grinding cycles for each catalyst. The structures were confirmed by x-ray diffraction.

EXAMPLE 9

Determination of Catalytic Activity

The reactor system employed in this example comprised essentially a reactor tube containing the catalyst. The tube was mounted in a controlled temperature furnace. One end of the tube was fed with the starting materials and at the other end the reaction products were withdrawn. The reactor was mounted to permit the upward flow of the reactants over a catalyst of one of Examples 1–8 with the products exiting into a gas chromatograph. Gas-phase samples were collected by air actuated sample valves in 1 cc loops. All the lines after the reactor were heated to prevent condensation. Samples were alternately collected before and after passing over the catalyst. This provided the reactant versus product analysis necessary for massbalancing the product stream.

A separately controlled furnace surrounded the concentric up-flow/plug-flow reactor. The temperature of the reactor was controlled by a set of manually operated potentiometers. These potentiometers were sequenced in turn by a clock-stepping switch. In this way a suitable sequence of temperatures was programmed. At each temperature, an exit followed by an inlet analysis was performed.

In a typical study the temperature was raised from room temperature to 300° C. under reactant feed. Samples were taken at several temperatures between 300° C. and 525° C. The product analysis was visually inspected to look for partial oxidation products. As soon as substantial conversion (usually of the limiting reactant—oxygen) was seen, the temperature was held constant for two or three analyses. Then the temperature was lowered again, in 20° increments, to 300° C. This last stage was usually done automatically. Following this, the specific partial oxidation activity was estimated both visually from the gas chromatographic analysis and by comparing the computer integrated gas chromatographic peaks. If warranted, the activity was checked at specific temperatures. Thermal restoration of activity was confirmed. The catalyst was removed from the furnace after cooling and replaced with a new catalyst to be studied.

Analysis was performed by a two column gas chromatographic unit. One column (molecular sieve) was used for the low boiling reactants and products ($N_2$, $O_2$, $CH_4$, CO) while the second column (10 feet or or 3.67 m PORAPAC Q packing at temperature ranging from 50° C. at the inlet to 210° C. at the outlet) was used for high boiling products. In addition to a dual pen recorder, an online computer (EAI) integrated the sample gas chromatographic peaks.

The gas chromatographic peak areas with appropriate sensitivity factors were fed into a mass-balancing computer program on a Modcomp computer performing a least squares fit of the input and output mass balance of the carbon atoms.

Representative results for various catalysts are presented in Tables 1–8.

The conversion indicates the percentage of propane that is converted over the catalyst. Of the propane converted, the amount that is totally oxidized to $CO_2$ is shown in the column "$CO_2$" and that oxidized to CO is shown in the next column headed "CO". The selectivity of the propane converted to partially oxidized hydrocarbons (alcohols, aldehydes, and ketones) and the selectivity of cracking are shown in the next two lines.

"Cracking" signifies the percentage of converted propane that forms propylene, ethylene, ethane or methane. The remaining converted propane is partially oxidized. Of the latter amount, the percentages of oxidation to specific products are shown in the next six lines.

TABLE 1

| $ZnTa_2O_6 \cdot 0.2VO_2$ Columbite | | | | | | |
|---|---|---|---|---|---|---|
| Temp °C. | 350 | 375 | 400 | 420 | 480 | 500 |
| Input HC/$O_2$ | 2/1 | 2/1 | 2/1 | 2/1 | 2/1 | 2/1 |
| Conversion (%) | 24 | 28 | 29 | 4 | 51 | 58 |
| Selectivity to | | | | | | |
| CO | 34 | 31 | 21 | 18 | 21 | 19 |
| $CO_2$ | 9 | 5 | 9 | 45 | 1.6 | 1 |
| Cracking | 29 | 44 | 53 | 8 | 71 | 74 |
| Partial Oxid | 28 | 20 | 17 | 29 | 6.4 | 6 |
| Specific Sel to | | | | | | |
| $CH_3OH$ | 42 | 53 | 47 | — | — | — |
| $CH_2O$ | 16 | 14 | 11 | 100 | — | — |
| $CH_3CH_2OH$ | — | — | — | — | 2 | 1 |
| $CH_3CHO$ | 40 | 31 | 40 | — | 22 | 24 |
| $CH_3CH_2CHO$ | 1 | 1 | 1 | — | 14 | 7 |
| $CH_2$=CHCHO | 1 | 1 | 1 | — | 62 | 68 |

TABLE 2

| $ZnTa_2O_6$ Columbite | | | |
|---|---|---|---|
| Temp °C. | Below 450° C. | 450° C. | 500° C. |
| Input HC/$O_2$ | 2/1 | 2/1 | 2/1 |
| Conversion | None | 2 | 33 |
| Selectivity to | | | |
| CO | — | 0.2 | 9 |
| $CO_2$ | — | 17 | 14 |
| Cracking | — | 49 | 70 |
| Partial Oxid | — | 34 | 6 |

TABLE 3

| $FeNb_2O_6 \cdot 0.2\ VO_2$ Columbite | | |
|---|---|---|
| Temp °C. | 382 | 474 |
| Input HC/$O_2$ | 2/1 | 2/1 |
| Conversion (%) | 18 | 23 |
| Selectivity to | | |
| CO | 47 | 29 |
| $CO_2$ | 7.5 | 5.7 |
| Cracking | 9.9 | 24 |
| Partial Oxid | 35.5 | 41.3 |
| Specific Sel to | | |
| $CH_3OH$ | 54 | 12 |
| $CH_2O$ | — | — |
| $CH_3CH_2OH$ | — | — |
| $CH_3CHO$ | 46 | 29 |
| $CH_3CH_2CHO$ | — | 26 |
| $CH_2$=CHCHO | — | 33 |

TABLE 4

| $NiTa_2O_6 \cdot 0.2VO_2$ - Trirutile | | |
|---|---|---|
| Temp °C. | 440 | 510 |
| Input HC/$O_2$ | 2/1 | 2/1 |
| Conversion (%) | 25 | 28 |
| Selectivity to | | |
| CO | 30 | 32 |
| $CO_2$ | 14 | 17 |
| Cracking | 36 | 38 |
| Partial Oxid | 20 | 13 |
| Specific Sel to | | |
| $CH_3OH$ | 31 | 34 |

TABLE 4 -continued

| NiTa$_2$O$_6$ . 0.2VO$_2$ - Trirutile | | |
|---|---|---|
| CH$_2$O | — | — |
| CH$_3$CH$_2$OH | — | — |
| CH$_3$CHO | 34 | 8 |
| CH$_3$CH$_2$CHO | 35 | 58 |
| CH$_2$=CHCHO | — | — |

TABLE 5

| NiTa$_2$O$_6$ - Trirutile | | |
|---|---|---|
| Temp °C. | 400 | 490 |
| Input HC/O$_2$ | 2/1 | 2/1 |
| Conversion | 0 | 0 |
| Selectivity to | | |
| CO | — | — |
| CO$_2$ | — | — |
| Cracking | — | — |
| Partial Oxid | — | — |

TABLE 6

| CoTa$_2$O$_6$ . 0.2VO$_2$ - Trirutile | | | |
|---|---|---|---|
| Temp °C. | 370 | 440 | 460 |
| Input HC/O$_2$ | 2/1 | 2/1 | 2/1 |
| Conversion (%) | 17 | 16 | 16 |
| Selectivity to | | | |
| CO | 22 | 21 | 24 |
| CO$_2$ | 25 | 33 | 32 |
| Cracking | 4 | 10 | 15 |
| Partial Oxid | 49 | 36 | 29 |
| Specific Sel to | | | |
| CH$_3$OH | 33 | 5 | 14 |
| CH$_2$O | 10 | 62 | 56 |
| CH$_3$CH$_2$OH | — | — | — |
| CH$_3$CHO | 10 | 7 | 30 |
| CH$_3$CH$_2$CHO | 47 | 26 | — |
| CH$_2$=CHCHO | — | — | — |

TABLE 7

| FeTa$_2$O$_6$ . 0.2 VO$_2$ - Trirutile | | | |
|---|---|---|---|
| Temp °C. | 320 | 380 | 480 |
| Input HC/O$_2$ | 2/1 | 2/1 | 2/1 |
| Conversion (%) | 14 | 21 | 44 |
| Selectivity to | | | |
| CO | 28 | 39 | 19 |
| CO$_2$ | 25 | 7 | 3 |
| Cracking | 4 | 10 | 66 |
| Partial Oxid | 43 | 44 | 12 |
| Specific Sel to | | | |
| CH$_3$OH | 23 | 36 | 10 |
| CH$_2$O | 32 | — | — |
| CH$_3$CH$_2$OH | — | — | — |
| CH$_3$CHO | 16 | 33 | 9 |
| CH$_3$CH$_2$CHO | — | — | 20 |
| CH$_2$=CHCHO | 28 | 31 | 61 |

TABLE 8

| Fe$_{1.5}$Nb$_{1.5}$O$_6$ . 0.2VO$_2$ - Rutile | | |
|---|---|---|
| Temp °C. | 370 | 475 |
| Input HC/O$_2$ | 2/1 | 2/1 |
| Conversion (%) | 19 | 42 |
| Selectivity to | | |
| CO | 37 | 24 |
| CO$_2$ | 12 | 1.2 |
| Cracking | 10 | 62 |
| Partial Oxid | 41 | 13 |
| Specific Sel to | | |
| CH$_3$OH | 43 | 10 |
| CH$_2$O | — | — |
| CH$_3$CH$_2$OH | — | 3 |

TABLE 8-continued

| Fe$_{1.5}$Nb$_{1.5}$O$_6$ . 0.2VO$_2$ - Rutile | | |
|---|---|---|
| CH$_3$CHO | 33 | 9 |
| CH$_3$CH$_2$CHO | 24 | 23 |
| CH$_2$=CHCHO | — | 55 |

We claim:

1. A method for producing oxidation products selected from the group consisting of alcohols, aldehydes, ketones and mixtures thereof from alkanes, comprises reacting an alkane at elevated temperatures within the range from about 300° C. to 600° C. with oxygen in the presence of a catalyst comprising a host-phase selected from the group consisting of niobates and tantalates of divalent and trivalent metals and containing vanadium from about 1 atom percent to the limit of solid solubility in the host phase.

2. The method of claim 1, wherein a host phase crystallizes with the trirutile structure.

3. The method of claim 1 wherein a host phase crystallizes with the rutile structure.

4. The method of claim 1 wherein a host phase crystallizes with the columbite structure.

5. The method of claim 1 wherein the vanadium content is from one to three atom percent.

6. The method of claim 1 wherein the ratio of oxygen in the catalyst to total metal is from about 1.8 to about 2.2 and the host phase is a niobate of a divalent metal.

7. The method of claim 1 wherein the ratio of oxygen in the catalyst to total metal is from about 1.8 to about 2.2 and the host phase is a tantalate of divalent metal.

8. The method of claim 6 or claim 7 wherein said ratio is from about 1.9 to about 2.1.

9. The method of claim 1 wherein said host phase is zinc tantalate.

10. The method of claim 1 wherein said host phase is iron (II) or iron (III) niobate.

11. The method of claim 1 wherein said host phase is nickel (II) tantalate.

12. The method of claim 1 wherein said host phase is cobalt (II) tantalate.

13. The method of claim 1 wherein said host phase is iron (II) or iron (III) tantalate.

14. The method of claim 9 or 10 or 11 or 12 or 13 wherein said catalyst contains between about 2 and about 10 atom percent vanadium.

15. The method of claim 1 wherein said catalyst is of one of the following formulae and phase structures:

| | |
|---|---|
| MNb$_2$O$_6$(VO$_2$)$_n$ | trirutile |
| MTa$_2$O$_6$(VO$_2$)$_n$ | trirutile |
| MNb$_2$O$_6$(VO$_2$)$_m$ | columbite |
| MTa$_2$O$_6$(VO$_2$)$_m$ | columbite |
| M$_{1.5}$Nb$_{1.5}$O$_6$(VO$_2$)$_p$ | rutile |
| M$_{1.5}$Ta$_{1.5}$O$_6$(VO$_2$)$_p$ | rutile | wherein n is between 0.1 and 0.2, m is between 0.01 and 1, p is between 0.01 and 0.5, M is a divalent metal selected from the grop consisting of Ca, Cd, Co, Fe, Mg, Mn, Ni and Zn, and said number n, m, or p is sufficiently small for VO$_2$ to be soluble in said structure formed by M, Ta or Nb and O.

16. The method of claim 1 wherein said catalyst is of one of the formulae:

N'NbO$_4$(VO$_2$)$_q$
M'TaO$_4$(VO$_2$)$_q$ wherein q is a number between 0.01 and 0.05 and M' is a trivalent metal selected from the group consisting of Cr, Fe, Mn and Al.

* * * * *